US012635969B2

(12) United States Patent (10) Patent No.: US 12,635,969 B2
Umekawa et al. (45) Date of Patent: May 26, 2026

(54) RADIOGRAPHIC IMAGING SYSTEM COMPRISING A RADIOGRAPHIC IMAGING APPARATUS, AND METHOD FOR CONTROLLING A RADIOGRAPHIC IMAGING APPARATUS

(71) Applicant: CANON KABUSHIKI KAISHA, Tokyo (JP)

(72) Inventors: Kazuaki Umekawa, Tokyo (JP); Katsuro Takenaka, Saitama (JP); Hiroyuki Tanaka, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 236 days.

(21) Appl. No.: 18/499,930

(22) Filed: Nov. 1, 2023

(65) Prior Publication Data

US 2024/0138799 A1 May 2, 2024

(30) Foreign Application Priority Data

Nov. 2, 2022 (JP) ................................ 2022-176233
Jul. 3, 2023 (JP) ................................ 2023-109517

(51) Int. Cl.
*A61B 6/40* (2024.01)
*A61B 6/00* (2006.01)
*A61B 6/42* (2024.01)
*G06T 7/00* (2017.01)

(52) U.S. Cl.
CPC ............ *A61B 6/545* (2013.01); *A61B 6/4233* (2013.01); *A61B 6/486* (2013.01); *A61B 6/5211* (2013.01); *A61B 6/541* (2013.01); *A61B 6/542* (2013.01); *G06T 7/0002* (2013.01); *G06T 2207/30168* (2013.01)

(58) Field of Classification Search
CPC ........... A61B 6/40; A61B 6/4085; A61B 6/42; A61B 6/4208; A61B 6/4233; A61B 6/4283; A61B 6/44; A61B 6/4452; A61B 6/486; A61B 6/487; A61B 6/488; A61B 6/52; A61B 6/5205; A61B 6/5211; A61B 6/54; A61B 6/542; A61B 6/545
USPC ................... 378/53, 54, 57, 58, 62, 108–112
See application file for complete search history.

(56) References Cited

U.S. PATENT DOCUMENTS

| | | | | |
|---|---|---|---|---|
| 5,282,254 A * | 1/1994 | Chiu | ...................... | A61B 6/542 |
| | | | | 382/199 |
| 5,369,678 A * | 11/1994 | Chiu | ...................... | A61B 6/487 |
| | | | | 378/158 |
| 8,879,689 B2 * | 11/2014 | Ohta | .................... | A61B 6/4233 |
| | | | | 378/97 |
| 8,903,048 B2 * | 12/2014 | Kitano | ................. | A61B 6/4233 |
| | | | | 378/115 |
| 8,971,494 B2 * | 3/2015 | Tajima | ................. | A61B 6/4283 |
| | | | | 378/96 |
| 9,006,675 B2 * | 4/2015 | Okada | .................... | G01T 1/243 |
| | | | | 250/394 |

(Continued)

FOREIGN PATENT DOCUMENTS

JP 2013033030 A 2/2013

*Primary Examiner* — Allen C. Ho
(74) *Attorney, Agent, or Firm* — Canon U.S.A., Inc. IP Division

(57) ABSTRACT
A radiographic imaging apparatus includes a plurality of pixels configured to convert radiation to electrical signals and a control section configured to determine an image capturing condition based on the electrical signals converted by the pixels and to start image capturing.

15 Claims, 7 Drawing Sheets

(56)                    References Cited

U.S. PATENT DOCUMENTS

| | | | | |
|---|---|---|---|---|
| 9,101,328 | B2 * | 8/2015 | Tsuji | A61B 6/542 |
| 9,265,467 | B2 * | 2/2016 | Kamiya | A61B 6/06 |
| 9,668,331 | B2 * | 5/2017 | Takahashi | A61B 6/542 |
| 9,750,477 | B2 * | 9/2017 | Kitagawa | A61B 6/5241 |
| 9,833,214 | B2 * | 12/2017 | Imamura | H04N 23/30 |
| 10,610,187 | B2 * | 4/2020 | Takeshima | A61B 6/542 |
| 11,369,332 | B2 * | 6/2022 | Kunieda | A61B 6/542 |
| 11,382,590 | B2 * | 7/2022 | Niwa | A61B 6/542 |
| 11,534,129 | B2 * | 12/2022 | Ohta | G01N 23/04 |
| 11,831,813 | B2 * | 11/2023 | Kawanabe | G01T 1/2018 |
| 11,831,994 | B2 * | 11/2023 | Watanabe | A61B 6/545 |
| 11,839,013 | B2 * | 12/2023 | Niwa | A61B 6/542 |
| 12,029,604 | B2 * | 7/2024 | Watanabe | A61B 6/586 |
| 12,059,287 | B2 * | 8/2024 | Uehara | A61B 6/545 |
| 12,167,926 | B2 * | 12/2024 | Nishii | A61B 6/465 |
| 12,242,004 | B2 * | 3/2025 | Sasaki | A61B 6/548 |
| 12,268,539 | B2 * | 4/2025 | Ueno | A61B 6/4447 |
| 12,274,570 | B2 * | 4/2025 | Tamura | A61B 6/4208 |
| 12,274,571 | B2 * | 4/2025 | Hayashida | A61B 6/542 |
| 12,295,779 | B2 * | 5/2025 | Taya | A61B 6/4035 |
| 12,303,317 | B2 * | 5/2025 | Umekawa | A61B 6/4291 |
| 12,357,262 | B2 * | 7/2025 | Odori | A61B 6/548 |

* cited by examiner

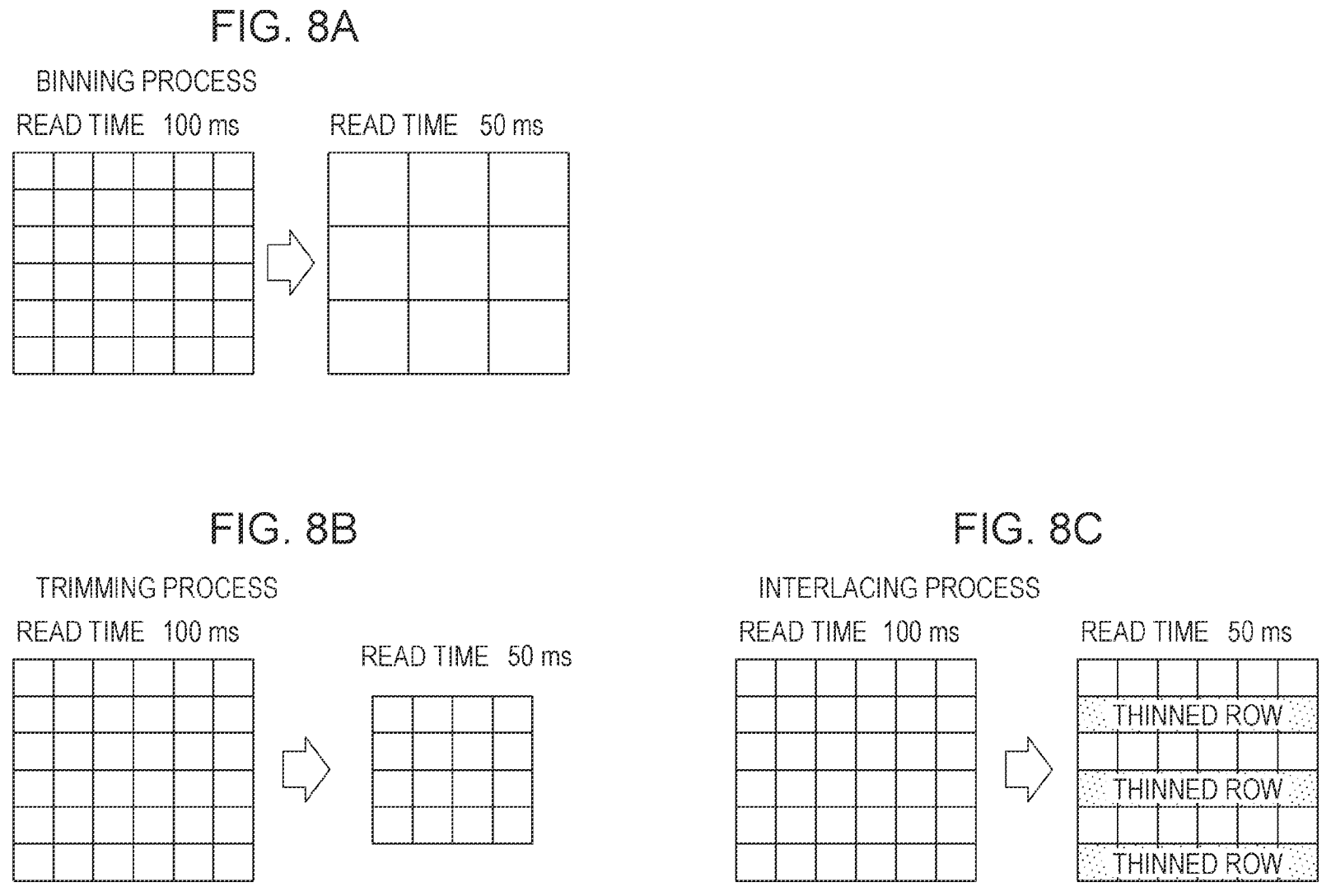

BINNING PROCESS

READ TIME 100 ms → READ TIME 50 ms

FIG. 8B

TRIMMING PROCESS

READ TIME 100 ms → READ TIME 50 ms

FIG. 8C

INTERLACING PROCESS

READ TIME 100 ms → READ TIME 50 ms

THINNED ROW

THINNED ROW

THINNED ROW

RADIOGRAPHIC IMAGING SYSTEM COMPRISING A RADIOGRAPHIC IMAGING APPARATUS, AND METHOD FOR CONTROLLING A RADIOGRAPHIC IMAGING APPARATUS

BACKGROUND OF THE DISCLOSURE

Field of the Disclosure

The present disclosure relates to radiographic imaging apparatuses, radiographic imaging systems, and methods for controlling the radiographic imaging apparatuses.

Description of the Related Art

Radiographic imaging apparatuses including a sensor panel that detects radiation, such as X-rays, are used in industrial, medical, and other fields. Expanding the functions of radiographic imaging apparatuses has recently been under consideration. In one example, a radiographic imaging apparatus having a built-in radiation monitoring function has been under consideration. This function allows the radiographic imaging apparatus to detect the timing when emission of radiation from the radiation source is started, the timing when emission of radiation is to be stopped, and a radiation dose or a cumulative radiation dose. The radiographic imaging apparatus can perform automatic exposure control (AEC) by detecting the cumulative dose of radiation that has passed through a subject and stopping the emission of radiation from the radiation source at the time when the detected cumulative dose has reached a proper amount.

Japanese Patent Laid-Open No. 2013-33030 discloses a radiographic imaging apparatus including image capturing pixels and radiation detection pixels and a method for detecting the timing when emission of radiation is started and the timing to stop the emission using the radiation detection pixels and instructing the radiation source to stop the emission.

Particularly in the industrial field, signal lines required for synchronous timing between the radiation source and the radiographic imaging apparatus are not connected, and image capturing is often performed asynchronously. The method disclosed in Japanese Patent Laid-Open No. 2013-33030 requires instructing the radiation source to stop emission, so that automatic exposure control is not available, and images cannot be captured at proper exposure.

SUMMARY OF THE DISCLOSURE

The present disclosure is directed to image capturing under correct image capturing conditions when radiographic imaging apparatuses capture images in asynchronization with a radiation source.

A radiographic imaging apparatus according to an aspect of the present disclosure includes a plurality of pixels configured to convert radiation to electrical signals and a control section configured to determine an image capturing condition based on the electrical signals converted by the pixels and to start image capturing.

Further features of the present disclosure will become apparent from the following description of exemplary embodiments with reference to the attached drawings.

BRIEF DESCRIPTION OF THE DRAWINGS

FIG. 2 is a diagram illustrating a configuration example of a radiographic imaging apparatus.

FIG. 8A is a diagram illustrating a binning process.

FIG. 8B is a diagram illustrating a trimming process.

FIG. 8C is a diagram illustrating an interlacing process.

DESCRIPTION OF THE EMBODIMENTS

First Embodiment

Figure 1:
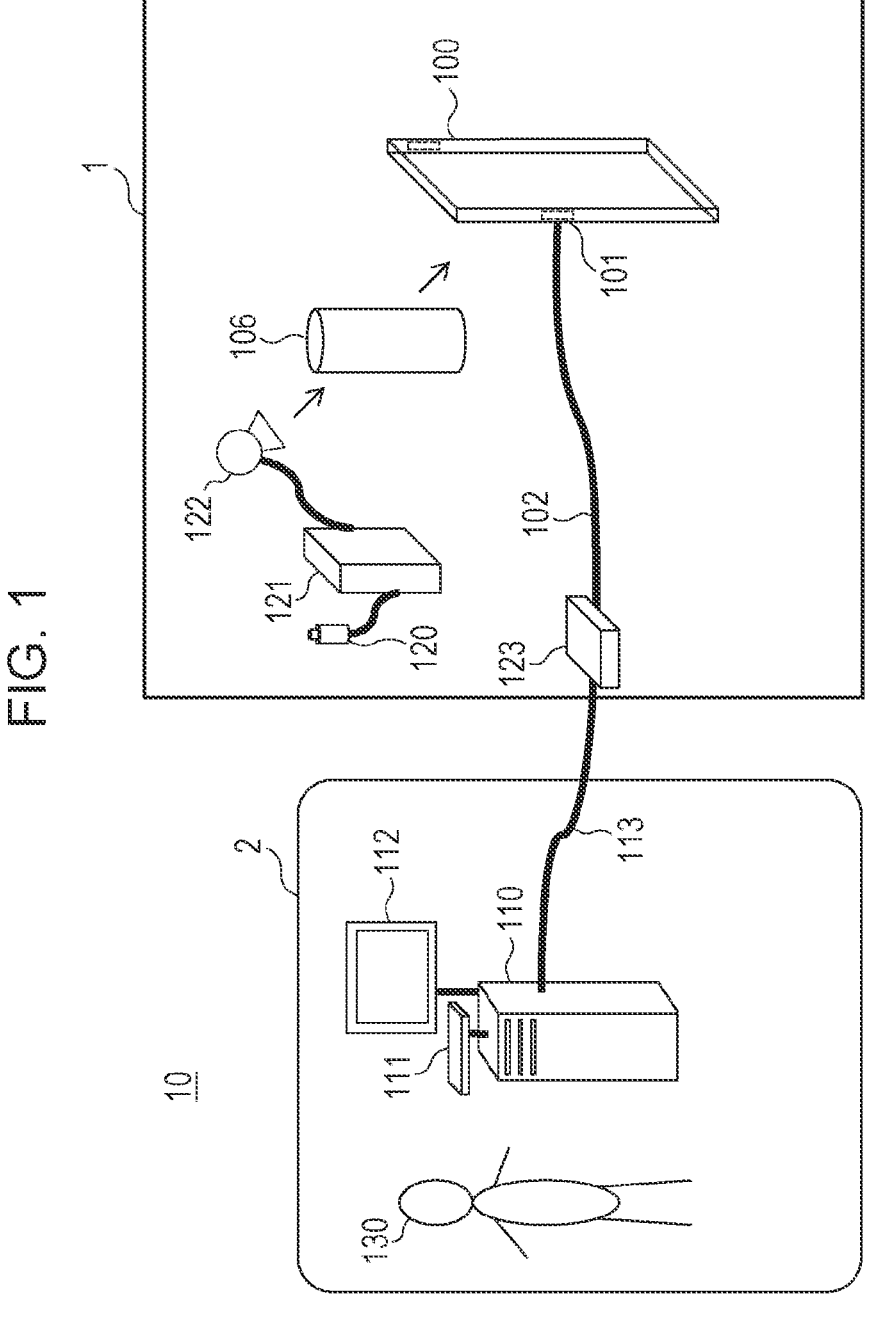
FIG. 1 is a diagram illustrating a configuration example of a radiographic imaging system.

FIG. 1 is a diagram illustrating a configuration example of a radiographic imaging system 10 according to a first embodiment. The radiographic imaging system 10 includes an image capturing section 1 and a control section 2. The image capturing section 1 performs emission of radiation and radiographic imaging. The radiation includes, X-rays, α-rays, β-rays, γ-rays, and various corpuscular rays.

The image capturing section 1 includes a radiographic imaging apparatus 100, a communication cable 102, a radiation switch 120, a radiation generating unit 121, a radiation source 122, and a communication controller 123. The control section 2 includes a controller 110, an input device 111, a display unit 112, and a communication cable 113.

The radiographic imaging apparatus 100 includes a wired communication unit 101. The radiographic imaging apparatus 100 detects radiation that has passed through a subject 106 and generates radiological image data. The radiographic imaging apparatus 100 connects to a power cable (not shown) and is supplied with power. The wired communication unit 101 communicates information via cable connection using a predetermined communication standard or the Ethernet.

The communication cable 102 is a cable for connecting the radiographic imaging apparatus 100 and the communication controller 123. The communication controller 123 controls communication between the radiographic imaging apparatus 100 and the controller 110.

The radiation generating unit 121 controls the radiation source 122 so as to emit radiation based on predetermined exposure conditions. The radiation source 122 is a radiating unit that applies radiation to the subject 106 under the control of the radiation generating unit 121.

The controller 110 communicates with the radiographic imaging apparatus 100 to control the radiographic imaging apparatus 100 via the communication controller 123.

The radiation switch 120 is connected to the radiation generating unit 121 and inputs the emission timing of radiation according to the operation of an operator 130. The input device 111 is a device that is connected to the controller 110 and that receives instructions from the operator 130. Examples include a keyboard and a touch panel. The display unit 112 is connected to the controller 110 and displays processed radiological image data and a graphical user interface (GUI) and includes a display.

Figure 2:
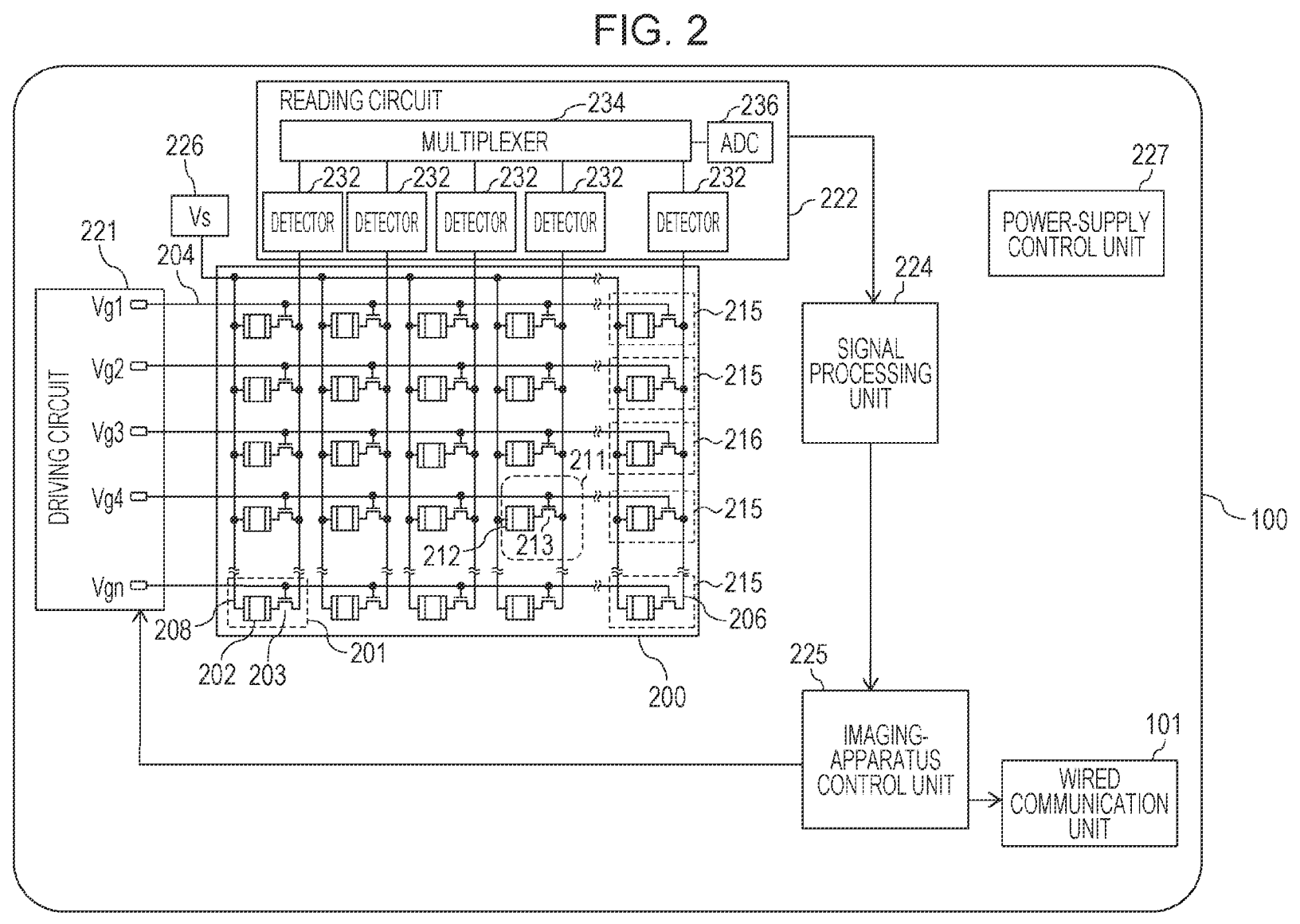

FIG. 2 is a diagram illustrating a configuration example of the radiographic imaging apparatus 100 in FIG. 1. The radiographic imaging apparatus 100 includes a radiation detector 200, a driving circuit 221, a reading circuit 222, a signal processing unit 224, an imaging-apparatus control unit 225, a power supply circuit 226, a power-supply control unit 227, and the wired communication unit 101.

The radiation detector 200 includes a plurality of pixels arranged in rows and columns to detect applied radiation. In the following description, a region of the radiation detector 200 in which the plurality of pixels is arrayed is referred to as "image capturing region". The plurality of pixels includes a plurality of detection pixels 201 and a plurality of correction pixels 211 each of which converts radiation to an electrical signal. The detection pixels 201 are pixels for generating radiological images or detecting radiation. The correction pixels 211 are pixels for removing a dark-current component and a crosstalk component.

Each of the plurality of detection pixels 201 includes a transducer 202 and a switch 203. The transducer 202 converts radiation to an electrical signal. The switch 203 is a switch for connecting a column signal line 206 and the transducer 202.

The transducer 202 includes a scintillator that converts radiation to light and a photoelectric conversion element that converts the light to an electrical signal and converts radiation to an electrical signal. The scintillator is formed like a sheet so as to cover the image capturing region and is shared by the plurality of pixels. The transducer 202 may include a transducer that directly converts radiation to an electrical signal to thereby convert radiation to an electrical signal.

The switch 203 includes a thin-film transistor (TFT) in which an active region is formed of a semiconductor, such as amorphous silicon or polycrystal silicon.

The detection pixels 201 are classified into normal pixels 215 and radiation-dose detection pixels 216 on a row-by-row manner. For example, the radiation-dose detection pixels 216 are the detection pixels 201 in the third line of voltage Vg3, and the normal pixels 215 are the detection pixels 201 in the other rows. The radiation-dose detection pixels 216 may be detection pixels 201 in a row other than the third row. The normal pixels 215 output radiological images based on incident radiation. The radiation-dose detection pixels 216 output radiation dose information based on incident radiation.

Each of the plurality of correction pixels 211 includes a transducer 212 and a switch 213. The transducer 212 has the same configuration as the transducer 202 and converts radiation to an electrical signal. The switch 213 is a switch that has the same configuration as the switch 203 and that connects the column signal line 206 and the transducer 212.

The correction pixels 211 have the same configuration as the detection pixels 201. However, the detection pixels 201 have a larger radiation detection region than the correction pixels 211. If the correction pixels 211 each have a direct transducer 212 that directly converts radiation to an electrical signal, a shielding member made of heavy metal, such as lead, for blocking radiation is provided on the transducer 212 of the correction pixel 211.

If the correction pixels 211 each have an indirect transducer 212 that converts radiation to light using a scintillator and then converts the light to an electrical signal, a shielding film, such as aluminum, is provided as a light blocking member between the transducer 212 of the correction pixel 211 and the scintillator.

The shielding member is disposed in a region of the image capturing region overlapping with at least part of the transducer 212 of the correction pixel 211 in plan view regardless of whether the transducer 212 is of a direct type or an indirect type.

The correction pixels 211 are shielded from radiation and detect a dark-current component or a crosstalk component. The detection pixels 201 output radiation dose information or radiological images based on the radiation. The signal processing unit 224 can generate accurate radiation dose information or radiological images by subtracting dark-current components or crosstalk components output from the correction pixels 211 from the radiation dose information or the radiological images output from the detection pixels 201.

The radiographic imaging apparatus 100 includes a plurality of column signal lines 206 and a plurality of drive lines 204.

The plurality of column signal lines 206 are individually connected in common to the pixels in the individual columns in the image capturing region.

The plurality of drive lines 204 are each connected in common to the pixels of the individual rows in the image capturing region. The driving circuit 221 supplies voltages Vg1 to Vgn to the plurality of pixels on a row-by-row manner via the plurality of drive lines 204.

A first electrode of the transducer 202 is connected to a first main electrode of the switch 203. A second electrode of the transducer 202 is connected to a bias line 208. One bias line 208 extends in the column direction and is connected in common to the second electrodes of the plurality of transducers 202 arrayed in the column direction. A second main electrodes of the switch 203 is connected to the column signal line 206.

A first electrode of the transducer 212 is connected to a first main electrode of the switch 213. A second electrode of the transducer 212 is connected to the bias line 208. One bias line 208 is connected in common to the second electrodes of the plurality of transducers 212 arrayed in the column direction. A second main electrodes of the switch 213 is connected to the column signal line 206.

The power supply circuit 226 supplies a bias voltage Vs to the bias lines 208. The power-supply control unit 227 includes the power supply circuit 226 and generates an analog-circuit supply voltage and a digital-circuit supply voltage for drive control, communication, and so on.

The second main electrodes of the switches 203 and 213 in the individual columns are connected to the column signal lines 206 of the individual columns. The control electrodes of the switches 203 and 213 in the individual rows are connected to the drive lines 204 of the individual rows. The plurality of column signal lines 206 are connected to the reading circuit 222.

The reading circuit 222 includes a plurality of detectors 232, a multiplexer 234, and an analog-to-digital converter (hereinafter referred to as an A/D converter) 236. The plurality of column signal lines 206 are individually connected to the plurality of detectors 232. One column signal line 206 is connected to one detector 232. The detectors 232 each include, for example, a differential amplifier and amplifies the signal from the column signal line 206. The multiplexer 234 selects the plurality of detectors 232 in a predetermined order and supplies a signal from the selected detector 232 to the A/D converter 236. The A/D converter 236 convers the supplied signal from analog to digital and outputs the digital signal. The A/D converter 236 has a plurality of sensitivity settings to amplify the digital signal.

The signal processing unit 224 outputs information on the radiation emitted to the radiographic imaging apparatus 100 based on the output signal from the A/D converter 236. Specifically, the signal processing unit 224 subtracts the dark-current component or the crosstalk component detected by the correction pixels 211 from the radiation information or the radiological image generated by the detection pixels 201.

The imaging-apparatus control unit 225 detects emission of radiation or calculates the radiation dose and cumulative radiation dose based on the information from the signal processing unit 224. The imaging-apparatus control unit 225 controls the driving circuit 221 and the reading circuit 222 based on the information from the signal processing unit 224 or a control command from the controller 110 in FIG. 1. The imaging-apparatus control unit 225 transmits the information from the signal processing unit 224 to the controller 110 via the wired communication unit 101.

Figure 3:
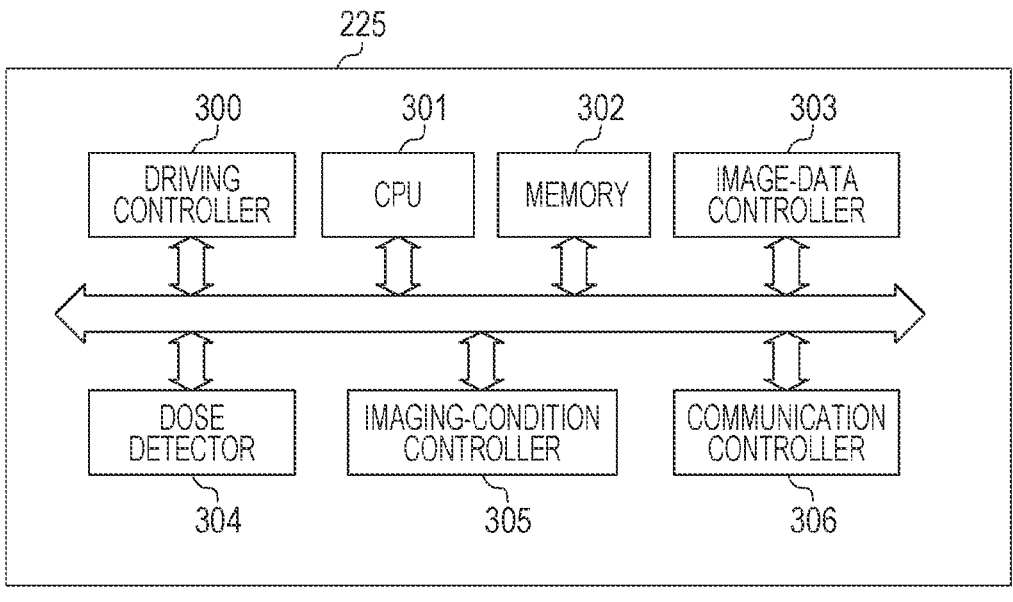
FIG. 3 is a block diagram illustrating a configuration example of an imaging-apparatus control unit according to a first embodiment.

FIG. 3 is a block diagram illustrating a configuration example of the imaging-apparatus control unit 225 in FIG. 2. The imaging-apparatus control unit 225 includes a driving controller 300, a central processing unit (CPU) 301, a memory 302, an image-data controller 303, a dose detector 304, an image-capturing-condition controller 305, and a communication controller 306.

The driving controller 300 controls the driving circuit 221 and the reading circuit 222 in FIG. 2 based on the information from the signal processing unit 224 in FIG. 2 or a command from the controller 110 in FIG. 1. The CPU 301 controls the entire radiographic imaging apparatus 100 using the programs and various data stored in the memory 302. The memory 302 stores, for example, programs for the CPU 301 to execute and various data. The various data includes various data obtained by the process of the CPU 301 and radiological image data. The image-data controller 303 stores the image data from the signal processing unit 224 in FIG. 2 in the memory 302.

The dose detector 304 detects the start of emission of radiation, a radiation dose, and a cumulative radiation dose based on the information from the signal processing unit 224 in FIG. 2 or the information from the driving controller 300. The dose detector 304 detects whether the emission of radiation is stable from the cumulative radiation dose of multiple frames.

The image-capturing-condition controller 305 sets image capturing conditions based on the detection result of the dose detector 304 and instructs the controller 110 to start to output images. The image capturing conditions include accumulation time (=frame rate), sensitivity, and the number of images to be captured.

The communication controller 306 starts to output images to the controller 110 via the wired communication unit 101 in response to the image output start instruction from the image-capturing-condition controller 305.

Next, the operation of the radiographic imaging system 10 will be described. The operator 130 sets information on the subject 106 to the controller 110 using the input device 111. The controller 110 gives an instruction, to the radiographic imaging apparatus 100, for an image capturing standby mode in which the radiation dose can be detected at a predetermined frame rate. The operator 130 sets a tube current, a tube voltage, and so on to the radiation generating unit 121. The radiation dose refers to the dose of radiation emitted from the radiation generating unit 121.

After the completion of the preparation for imaging, the operator 130 presses the radiation switch 120. When the radiation switch 120 is pressed, the radiation source 122 emits radiation toward the subject 106 under the control of the radiation generating unit 121. The radiation applied to the subject 106 passes through the subject 106 into the radiographic imaging apparatus 100. The radiographic imaging apparatus 100 drives a designated drive line 204 with the driving circuit 221. A plurality of detection pixels 201 corresponding to the designated drive line 204 detects the dose (radiation dose) and outputs the radiation dose information. The imaging-apparatus control unit 225 calculates the cumulative radiation dose, which is a cumulative dose detected by the detection pixels 201 in a predetermined frame rate period, to detect the cumulative radiation dose of each frame and determines whether the cumulative radiation dose has become stable. After determining that the cumulative radiation dose has become stable, the imaging-apparatus control unit 225 performs image capturing settings (accumulation time, sensitivity, and the number of frames) for proper exposure based on the cumulative radiation dose.

After the image capturing settings, the detection pixels 201 converts the radiation to electrical signals to generate radiological image signals. The A/D converter 236 converts the analog radiological image signals to digital radiological image data. The signal processing unit 224 subtracts a dark-current component or a crosstalk component from the radiological image data to generate accurate radiological image data. The imaging-apparatus control unit 225 transmits the generated digital radiological image data to the controller 110 via the communication cable 102, the communication controller 123, and the communication cable 113.

The controller 110 performs image processing on the received radiological image data. For example, the controller 110 averages the received radiological image data of multiple frames to generate a radiological image.

The controller 110 displays the generated radiological image on the display unit 112. The controller 110 also functions as an image processing unit and a display controller.

Figure 4:
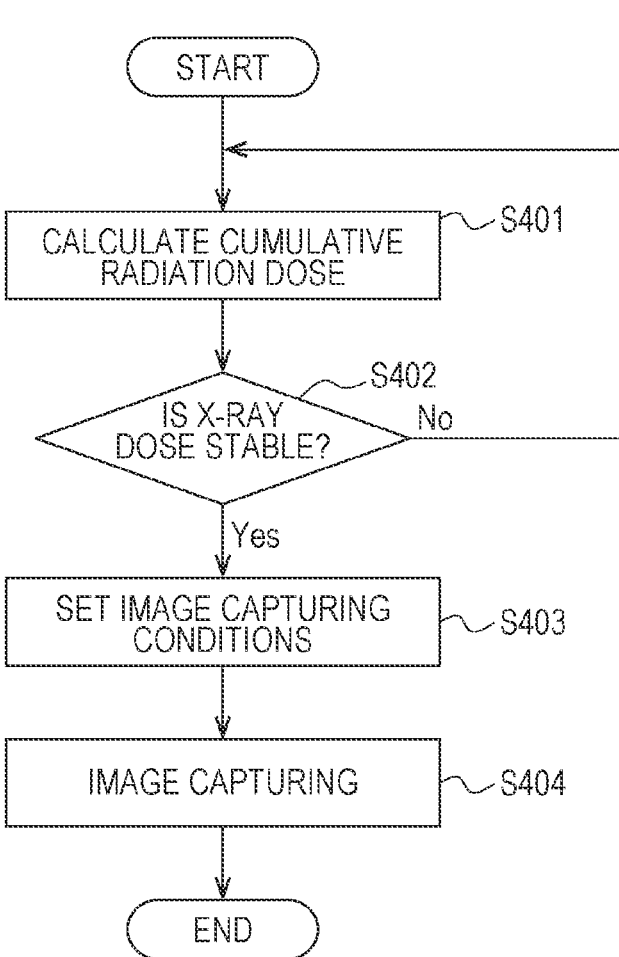
FIG. 4 is a flowchart for a method for controlling the radiographic imaging apparatus.

FIG. 4 is a flowchart for a method for controlling the radiographic imaging apparatus 100. In step S401, the driving controller 300 in the radiographic imaging apparatus 100 starts the driving so as to detect the radiation dose. To quickly confirm that the radiation dose has become stable, the driving controller 300 performs the driving, for example, with the settings of a frame rate of 10 FPS, an accumulation time of 100 ms, and 2× sensitivity for amplifying the digital signals with the A/D converter 236. The dose detector 304 calculates the cumulative radiation dose every frame (100 ms). The cumulative radiation dose is the integrated value of the doses that the detection pixels 201 of the radiographic imaging apparatus 100 have detected in a predetermined frame rate period.

The specific process of step S401 will be described. The detection pixels 201 and the correction pixels 211 are hereinafter collectively referred to as pixels. The driving circuit 221 turns on the switches of the pixels in rows 1 to n in order row by row to output pixel signals. The normal pixels 215 are switched on once in one frame and output signals to the column signal lines 206 once. The radiation-dose detection pixels 216 are switched on a plurality of times in one frame and output signals to the column signal lines 206 a plurality of times. For example, in the third row, the signal processing unit 224 subtracts the signals of the correction pixels 211 from the signals of the radiation-dose detection pixels 216 and outputs the subtracted signals to the imaging-apparatus control unit 225. The dose detector 304 in the imaging-apparatus control unit 225 integrates the plurality of signals of the radiation-dose detection pixels 216 after the subtraction and averages the integrated signals of the radiation-dose detection pixels 216 as a cumulative radiation dose.

In step S402, the dose detector 304 determines whether the radiation dose has become stable.

For example, when the difference in cumulative radiation dose between the latest three frames falls within ±5%, the dose detector 304 determines that the cumulative radiation dose has become stable. If it is determined that the cumulative radiation dose has become stable, the process goes to step S403. If it is determined that the cumulative radiation dose has not become stable, the process returns to step S401, and the cumulative radiation dose of the next frame is calculated.

In step S403, the image-capturing-condition controller 305 determines image capturing conditions based on the information on the cumulative radiation dose calculated in step S401 and performs drive setting on the driving controller 300. For example, the image-capturing-condition controller 305 sets sensitivity, accumulation time (=frame rate), and the number of images to be captured. The image-capturing-condition controller 305 sets the sensitivity for amplifying the digital signals with the A/D converter 236 to 1×. Assuming that the proper exposure of the subject 106 is set to 25,000 LSB (in the case of a depth of 16 bits) as the pixel value of the radiological image, if ten times the cumulative radiation dose is required, the sensitivity is set at half. For this reason, the image-capturing-condition controller 305 sets the frame rate to 0.5 FPS, and the accumulation time to 2,000 ms. To reduce the system noise, the image-capturing-condition controller 305 sets the number of images to be captured to 10.

In step S404, the CPU 301 starts image capturing under the image capturing conditions set in step S403 and transmits the radiological image data generated by the image-data controller 303 to the controller 110 via the communication controller 306. The driving controller 300 performs the driving, for example, with the settings of a frame rate of 0.5 FPS, an accumulation time of 2,000 ms, and 1× sensitivity for amplifying the digital signals with the A/D converter 236.

The specific process of step S404 will be described below. The driving circuit 221 turns on the switches of the pixels in rows 1 to n in order row by row to output pixel signals. The normal pixels 215 are switched on once in one frame and output signals to the column signal lines 206 once. The radiation-dose detection pixels 216 are switched on a plurality of times in one frame and output signals to the column signal lines 206 a plurality of times. The signal processing unit 224 subtracts the signals of the correction pixels 211 from the signals of the normal pixels 215 row by row and outputs the subtracted signals to the imaging-apparatus control unit 225. The CPU 301 in the imaging-apparatus control unit 225 transmits, as radiological image data, the signals of the normal pixels 215 after the subtraction to the controller 110 every frame (2,000 ms).

After the number of images set in step S403 have been captured, the CPU 301 stops the transmission of the radiological image data. The controller 110 generates a radiological image obtained by averaging the received radiological image data of the multiple frames and displays the radiological image on the display unit 112.

In the above example, the image-capturing-condition controller 305 sets the number of images to be captured to two or more to reduce the system noise. However, if the system noise is within an acceptable range, the number of images to be captured may be set to one.

Figure 5:
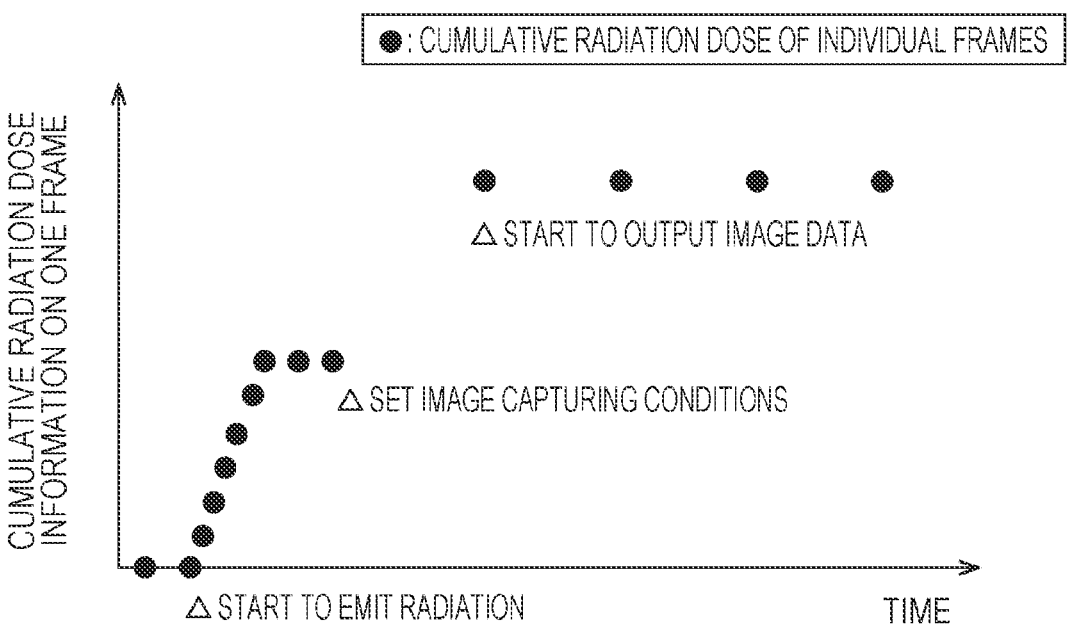
FIG. 5 is a graph showing cumulative radiation dose information on the individual frames during emission of radiation.

FIG. 5 is a graph showing the cumulative radiation dose information on individual frames during emission of radiation. The cumulative radiation dose in one frame is 0 before emission of radiation is started and increases when emission of radiation is started. Some radiation generating units 121 require several seconds until emission of radiation becomes stable, depending on the performance. The image-capturing-condition controller 305 sets image capturing conditions required for proper exposure based on the cumulative radiation dose at the timing at which the cumulative radiation dose in one frame stops increasing. In FIG. 5, the cumulative radiation dose necessary for proper exposure is set to 2×. Image data in which the detected cumulative radiation dose information is doubled in accordance with the set image capturing conditions is output.

The dose detector 304 determines whether the radiation emission has become stable, as described above. The image-capturing-condition controller 305 sets image capturing conditions under which the subject 106 is properly exposed. When the CPU 301 starts image capturing, a properly exposed radiological image can be obtained.

Although, in step S403, the image-capturing-condition controller 305 sets sensitivity, accumulation time, and the number of images to be captured, binning may be added to set image capturing conditions for proper exposure. In FIG. 2, the radiographic imaging apparatus 100 detects the radiation dose using the detection pixels 201 and the correction pixels 211 but may use only the pixels that detect the radiation dose.

The radiographic imaging apparatus 100 is supposed to obtain an image for offset correction to remove a dark-current component in the radiological image while no radiation is emitted. The radiographic imaging apparatus 100 may obtain the offset correction image before the radiographic imaging apparatus 100 is instructed to prepare for image capturing by the controller 110. Alternatively, the radiographic imaging apparatus 100 may obtain the offset correction image until the radiation dose is detected during preparation for image capturing.

In step S402, if the radiation dose has become stable but the detected cumulative radiation dose is small, so that a cumulative radiation dose necessary for proper exposure is not satisfied, the radiographic imaging apparatus 100 notifies the controller 110 of it. A message to prompt the operator 130 to change the settings of the radiation generating unit 121, such as the tube current or the tube voltage, may be displayed on the display unit 112. The same applies to a case in which the cumulative radiation dose is saturated.

If the subject 106 is small for the radiographic imaging apparatus 100, the controller 110 may give an instruction for a radiation dose detection area to the radiographic imaging apparatus 100 so that the radiation dose can be detected only for the area of the subject 106.

In step S402, it is determined that the radiation dose has become stable from a change in radiation dose information. Alternatively, if the time when the radiation dose will become stable can be specified owing to the characteristics of the radiation generating unit 121, it may be determined that the radiation dose has become stable after the lapse of a predetermined time (for example, five seconds) from the start of emission of radiation.

If the user can determine that the radiation dose has become stable from, for example, the display related to the radiation generating unit 121, the user may communicate with the radiographic imaging apparatus 100 using the input device 111 so that the radiographic imaging apparatus 100 can determine that the radiation dose has become stable.

The radiographic imaging apparatus 100 includes a plurality of pixels for converting the radiation to electrical signals, as described above. The pixels include the radiation-dose detection pixels 216. The imaging-apparatus control unit 225 determines image capturing conditions based on the electrical signals converted by the pixels and starts image capturing. Specifically, the imaging-apparatus control unit 225 determines the image capturing conditions based on the dose information on the incident radiation based on the electrical signals converted by the pixels.

In step S402, when the difference in radiation dose information between a plurality of frames before the current frame falls within a predetermined range, the imaging-apparatus control unit 225 determines that the radiation dose has become stable. The imaging-apparatus control unit 225 may determine that the radiation dose has become stable when the inclination of the difference in radiation dose information between the immediately preceding frame and the current frame falls within the predetermined range.

In step S403, the imaging-apparatus control unit 225 determines the image capturing conditions based on the radiation dose information when the radiation dose has become stable. The imaging-apparatus control unit 225 determines any of the sensitivity, the accumulation time, the frame rate, and the number of images to be captured as the image capturing conditions.

If the time when the radiation dose will become stable can be specified owing to the characteristics of the radiation generating unit 121, the imaging-apparatus control unit 225 may determine that the radiation dose has become stable after the lapse of a predetermined time (for example, five seconds) from the start of emission of radiation. In this case, the imaging-apparatus control unit 225 determines the image capturing conditions based on the radiation dose information after the lapse of the predetermined time after the start of emission of radiation is determined based on the radiation dose information.

If the user can determine that the radiation dose has become stable from, for example, the display related to the radiation generating unit 121, the user may communicate with the radiographic imaging apparatus 100 using the input device 111 so that the radiographic imaging apparatus 100 can determine that the radiation dose has become stable. In this case, the imaging-apparatus control unit 225 determines the image capturing conditions based on the radiation dose information when the information based on the user's operation is received.

In step S401 before the radiation dose becomes stable, the imaging-apparatus control unit 225 obtains the radiation dose information with the settings of a higher frame rate and higher sensitivity than in step S404 after the radiation dose has become stable and does not output images. This allows, in step S402, the imaging-apparatus control unit 225 to early determine that the radiation does has become stable.

The imaging-apparatus control unit 225 outputs no image in step S401 before the radiation dose becomes stable, and in step S403 after the radiation dose has become stable, determines the image capturing conditions, and in step S404 after the image capturing conditions are determined, outputs the captured image.

Thus, according to this embodiment, in image capturing, with the radiation source 122 and the radiographic imaging apparatus 100 in asynchronization, the radiographic imaging apparatus 100 can capture images at proper exposure.

Second Embodiment

A second embodiment illustrates the operation of determining image capturing conditions from image information and starting image capturing. The image information here refers to radiological image data.

The configuration of a radiographic imaging system 10 of the second embodiment is the same as the configuration of the first embodiment in FIG. 1, and the configuration of a radiographic imaging apparatus 100 of the second embodiment is the same as the configuration in FIG. 2. Differences of the second embodiment from the first embodiment will be described hereinbelow.

Figure 6:
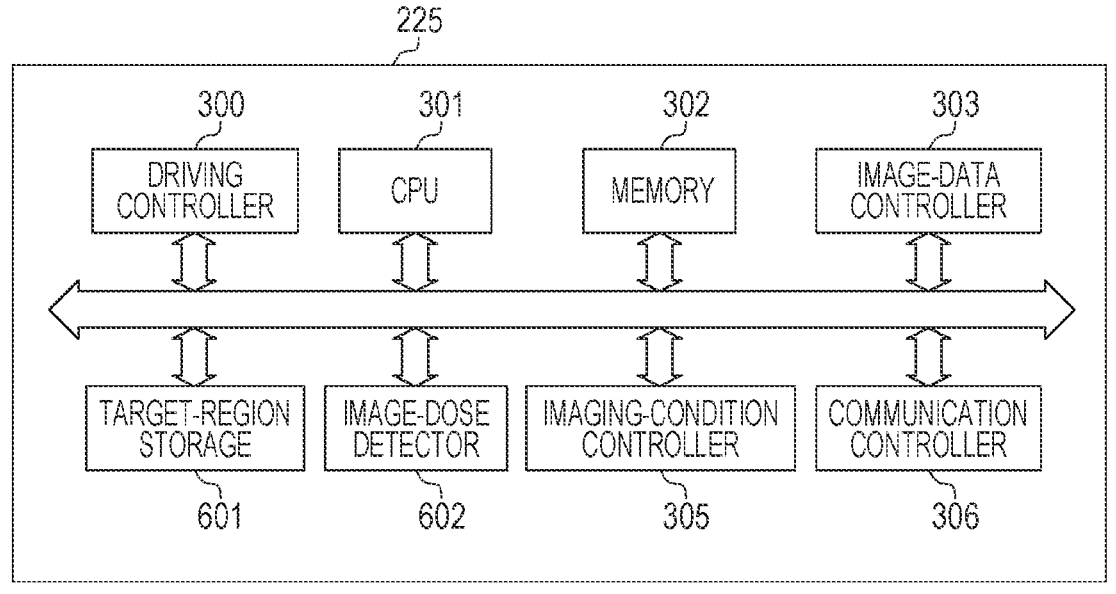
FIG. 6 is a diagram illustrating a configuration example of an imaging-apparatus control unit according to a second embodiment.

FIG. 6 is a diagram illustrating a configuration example of an imaging-apparatus control unit 225 in FIG. 2 according to the second embodiment.

The imaging-apparatus control unit 225 in FIG. 6 excludes the dose detector 304 from the imaging-apparatus control unit 225 in FIG. 3 and additionally includes a target-region storage 601 and an image dose detector 602.

The imaging-apparatus control unit 225 in FIG. 6 includes a driving controller 300, a CPU 301, a memory 302, an image-data controller 303, a target-region storage 601, an image dose detector 602, an image-capturing-condition controller 305, and a communication controller 306.

The driving controller 300 controls the driving circuit 221 and the reading circuit 222 in FIG. 2 based on the information from the signal processing unit 224 in FIG. 2 or a command from the controller 110 in FIG. 1. The CPU 301 controls the entire radiographic imaging apparatus 100 using the programs and various data stored in the memory 302. The memory 302 stores, for example, programs for the CPU 301 to execute and various data. The various data includes various data obtained by the process of the CPU 301 and radiological image data. The image-data controller 303 stores the image data from the signal processing unit 224 in FIG. 2 in the memory 302.

The CPU 301 or the image dose detector 602 detects the start of emission of radiation and a radiation dose based on the information from the signal processing unit 224 in FIG. 2, the information from the driving controller 300, the image information from the image-data controller 303, or the target region information from the target-region storage 601. The CPU 301 or the image dose detector 602 determines whether the emission of radiation is stable from the image information on multiple frames.

The image-capturing-condition controller 305 sets image capturing conditions based on the detection result of the CPU 301 or the image dose detector 602 and instructs the controller 110 to start to output images. The image capturing conditions include accumulation time (=frame rate), sensitivity, and the number of images to be captured.

The communication controller 306 starts to output images to the controller 110 via the wired communication unit 101 in response to the image output start instruction from the image-capturing-condition controller 305.

Next, the operation of the radiographic imaging system 10 will be described. The operator 130 sets information on the subject 106 and target region information stored in the target-region storage 601 to the controller 110 using the input device 111. The controller 110 gives an instruction, to the radiographic imaging apparatus 100, for an image capturing standby mode in which the radiation dose can be detected at a predetermined frame rate. The operator 130 sets a tube current, a tube voltage, and so on to the radiation generating unit 121. The radiation dose refers to the dose of radiation emitted from the radiation generating unit 121.

After the completion of the preparation for imaging, the operator 130 presses the radiation switch 120. When the radiation switch 120 is pressed, the radiation source 122 emits radiation toward the subject 106 under the control of the radiation generating unit 121. The radiation applied to the subject 106 passes through the subject 106 into the radiographic imaging apparatus 100. The radiographic imaging apparatus 100 drives a designated drive line 204 with the driving circuit 221. A plurality of detection pixels 201 corresponding to the designated drive line 204 detects the dose (radiation dose) and outputs the radiation dose information. The imaging-apparatus control unit 225 calculates the average value of the pixels values of the target region in the radiation image captured in a predetermined frame rate period and compares the average value with the average value of the pixel values of the target region in the radiation image of the preceding frame to determine whether the pixel values of the target region have become stable. After determining that a change in the average values of the pixel values of the target regions compared is small and the pixel values have become stable, the imaging-apparatus control unit 225 performs image capturing settings (accumulation time, sensitivity, and the number of frames) for proper exposure based on the image information.

After the image capturing settings, the detection pixels 201 converts the radiation to electrical signals to generate radiological image signals. The A/D converter 236 converts the analog radiological image signals to digital radiological image data. The signal processing unit 224 subtracts a dark-current component or a crosstalk component from the radiological image data to generate accurate radiological image data. The imaging-apparatus control unit 225 transmits the generated digital radiological image data to the controller 110 via the communication cable 102, the communication controller 123, and the communication cable 113.

The controller 110 performs image processing on the received radiological image data. For example, the controller 110 averages the received radiological image data of multiple frames to generate a radiological image.

The controller 110 displays the generated radiological image on the display unit 112. The controller 110 also functions as an image processing unit and a display controller.

Figure 7:
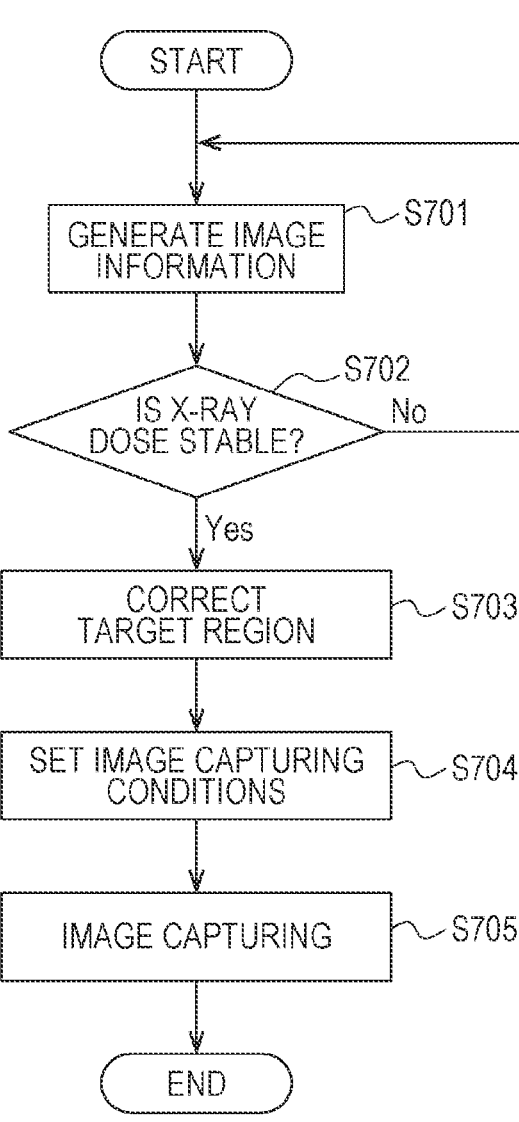
FIG. 7 is a flowchart for a method for controlling the radiographic imaging apparatus.

FIG. 7 is a flowchart for a method for controlling the radiographic imaging apparatus 100 according to the second embodiment.

In step S701, the radiographic imaging apparatus 100 generates image information frame by frame. To quickly confirm that the image information has become stable, the signal processing unit 224 performs 2×2 binning as in FIG. 8A. This allows the driving controller 300 to perform the driving, for example, with the settings of a frame rate of 20 FPS, an accumulation time of 50 ms, and 2× sensitivity for amplifying the digital signals with the A/D converter 236. If the 2×2 binning is not performed, the time for the imaging-apparatus control unit 225 to read image information from the signal processing unit 224 is 100 ms and the frame rate is 10 FPS. In contrast, if the 2×2 binning is performed, the time for the imaging-apparatus control unit 225 to read image information from the signal processing unit 224 is 50 ms and the frame rate is 20 FPS.

The signal processing unit 224 may increase the frame rate by the trimming in FIG. 8B or the interlacing in FIG.

8C, instead of the 2×2 binning in FIG. 8A. Increasing the frame rate can decrease the time from the image capturing in step S701 to the determination in step S702.

The trimming in FIG. 8B is a process for increasing the frame rate by the signal processing unit 224 outputting only part of the radiological image. The interlacing in FIG. 8C is a process for increasing the reading speed by scanning not all the drive lines 204 but every several drive lines 204 with the driving circuit 221.

In step S702, the dose detector 304 determines whether the image information output from the signal processing unit 224 has become stable. Specifically, the image dose detector 602 calculates the average value of the pixel values of the image information output from the signal processing unit 224. For example, if the difference between the average values of the pixel values of the image information of the latest three frames falls within ±5%, the image dose detector 602 determines that the image information has become stable. If the image dose detector 602 determines that the image information has become stable, the image dose detector 602 records the average value as radiation dose information, and the process goes to step S703. If the image dose detector 602 determines that the image information has not become stable, the process returns to step S701, and the mage information of the next frame is generated.

The image dose detector 602 may calculate the average value of the pixel values of the target region in the image information output from the signal processing unit 224. For example, if the difference between the average values of the pixel values of the target region in the image information of the latest three frames is within ±5%, the image dose detector 602 determines that the image information has become stable. If the image information is determined to have become stable, the image dose detector 602 stores the average value as stable radiation dose information, and the process goes to step S703. If the image information is determined not to have become stable, the process returns to step S701.

In step S703, if the target region is to be corrected from the displayed radiological image, the imaging-apparatus control unit 225 corrects the target region information stored in the target-region storage 601.

In step S704, the image-capturing-condition controller 305 determines image capturing conditions based on the image information generated in step S701 and performs drive settings on the driving controller 300. The image-capturing-condition controller 305 may determine the image capturing conditions based on the pixel values of the target region in the image information and perform the drive settings on the driving controller 300.

For example, the image-capturing-condition controller 305 sets sensitivity, accumulation time (=frame rate), and the number of images to be captured. To capture the images at high resolution and low gain, the image-capturing-condition controller 305 terminates the binning of the signal processing unit 224 and sets the sensitivity for amplifying the digital signals with the A/D converter 236 to 1×. In this case, since the sensitivity is one-eighth, multiplying the accumulation time by 8 yields the same average pixel value.

If the stable radiation dose information stored is 12,500 LSB, and the proper exposure to the subject 106 to be imaged is 25,000 LSB (a length of 16 bits), a double dose has to be emitted. To obtain the same pixel values as before the change in settings, the image-capturing-condition controller 305 sets the accumulation time to 50 ms×8×2=800 ms because the accumulation time is eight times and a double does is required. The image-capturing-condition controller 305 sets the number of images to be captured to 10 to reduce the system noise.

In step S705, the CPU 301 starts image capturing under the image capturing conditions set in step S704 to transmit the image information generated by the image-data controller 303 to the controller 110 via the communication controller 306. For example, the driving controller 300 performs the driving, for example, with the settings of an accumulation time of 800 ms and 1× sensitivity for amplifying the digital signals with the A/D converter 236.

The CPU 301 stops the transmission of the image information after the number of images set in step S704 have been captured. The controller 110 generates a radiological image in which the image information of the plurality of frames received is averaged and displays the radiological image on the display unit 112.

In the above example, the image-capturing-condition controller 305 sets the number of images to be captured to two or more to reduce the system noise but may set the number of images to be captured to one.

The image dose detector 602 determines whether the image information has become stable, as described above. The image-capturing-condition controller 305 sets image capturing conditions under which the subject 106 is properly exposed. When the CPU 301 starts image capturing, a properly exposed radiological image can be obtained.

Although, in step S704, the image-capturing-condition controller 305 sets sensitivity, accumulation time, and the number of images to be captured, binning may be added to set image capturing conditions for proper exposure.

The radiographic imaging apparatus 100 is supposed to obtain an image for offset correction to remove a dark-current component in the radiological image while no radiation is emitted. The radiographic imaging apparatus 100 may obtain the offset correction image before the radiographic imaging apparatus 100 is instructed to prepare for image capturing by the controller 110. Alternatively, the radiographic imaging apparatus 100 may obtain the offset correction image until a change in image information is detected during preparation for image capturing.

In step S702, if the image information has become stable but the value of the stable dose information on the target region in the image information is small, so that a proper exposure dose is not satisfied, the radiographic imaging apparatus 100 notifies the controller 110 of it. A message to prompt the operator 130 to change the settings of the radiation generating unit 121, such as the tube current or the tube voltage, may be displayed on the display unit 112. The same applies to a case in which the pixel values in the target region are saturated.

If the subject 106 is small for the radiographic imaging apparatus 100, the controller 110 may give an instruction for an image information generation area to the radiographic imaging apparatus 100 so that the image information can be generated only for the area of the subject 106

In step S702, it is determined that the image information has become stable from a change in image information. Alternatively, if the time when the image information will become stable can be specified owing to the characteristics of the radiation generating unit 121, it may be determined that the image information has become stable after the lapse of a predetermined time (for example, five seconds) from the start of emission of radiation.

If the user can determine that the image information has become stable from, for example, the display related to the radiation generating unit 121, the user may communicate with the radiographic imaging apparatus 100 using the input device 111 so that the radiographic imaging apparatus 100 can determine that the image information has become stable.

The radiographic imaging apparatus 100 includes a plurality of pixels for converting the radiation to electrical signals, as described above. The imaging-apparatus control unit 225 determines image capturing conditions based on the electrical signals converted by the pixels. The image information may be the pixel values of the target region in the image information.

In step S702, when the difference in image information between a plurality of frames before the current frame falls within a predetermined range, the imaging-apparatus control unit 225 determines that the image information has become stable. The imaging-apparatus control unit 225 may determine that the image information has become stable when the inclination of the difference in image information between the immediately preceding frame and the current frame falls within the predetermined range. The image information may be the pixel values of the target region in the image information.

In step S704, the imaging-apparatus control unit 225 determines the image capturing conditions based on the image information when the image information has become stable. The imaging-apparatus control unit 225 determines any of the sensitivity, the accumulation time, the frame rate, and the number of images to be captured as the image capturing conditions. The image information may be the pixel values of the target region in the image information.

If the time when the image information will become stable can be specified owing to the characteristics of the radiation generating unit 121, the imaging-apparatus control unit 225 may determine that the image information has become stable after the lapse of a predetermined time (for example, five seconds) from the start of emission of radiation. In this case, the imaging-apparatus control unit 225 determines the image capturing conditions based on the image information after the lapse of the predetermined time after the start of emission of radiation is determined based on the image information.

If the user can determine that the image information has become stable from, for example, the display related to the radiation generating unit 121, the user may communicate with the radiographic imaging apparatus 100 using the input device 111 so that the radiographic imaging apparatus 100 can determine that the image information has become stable. In this case, the imaging-apparatus control unit 225 determines the image capturing conditions based on the image information when the information based on the user's operation is received.

In step S701 before the image information becomes stable, the imaging-apparatus control unit 225 starts image capturing with the settings of a higher frame rate and higher sensitivity than in step S705 after the image information has become stable. This allows, in step S702, the imaging-apparatus control unit 225 to early determine that the image information has become stable.

Thus, according to this embodiment, in image capturing, with the radiation source 122 and the radiographic imaging apparatus 100 in asynchronization, the radiographic imaging apparatus 100 can capture images at proper exposure.

A comparison between the method for determining whether radiation has become stable from the radiation dose information calculated using the correction pixels 211 in the first embodiment and the method for determining whether the radiation has become stable from the image information in the second embodiment shows that the first embodiment has the advantage that the high time resolution allows image capturing to be started by changing the settings at an earlier stage and that the second embodiment has the advantages that the target region can be freely set to obtain the image information and the correction pixels 211 are not needed because not the radiation dose information on only the region of the correction pixels 211 is obtained but all the radiological images can be obtained.

According to embodiments of the present disclosure, the radiographic imaging apparatus can perform image capturing under proper image capturing conditions when performing image capturing asynchronously with the radiation source.

Other Embodiments

Embodiment(s) of the present disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2022-176233, filed Nov. 2, 2022, and No. 2023-109517, filed Jul. 3, 2023, which are hereby incorporated by reference herein in their entirety.

What is claimed is:

1. A radiographic imaging apparatus comprising:
a plurality of pixels configured to convert radiation to electrical signals; and
a control section configured to determine an image capturing condition based on the electrical signals converted by the plurality of pixels and to start image capturing,

wherein the control section further determines the image capturing condition based on incident-radiation dose information based on the electrical signals converted by the plurality of pixels, and
wherein the control section further determines the image capturing condition based on radiation dose information when a radiation dose has become stable.

2. The radiographic imaging apparatus according to claim 1, wherein the control section determines, as the image capturing condition, a sensitivity, an accumulation time, a frame rate, or a number of images to be captured.

3. The radiographic imaging apparatus according to claim 1, wherein, when a difference in radiation dose information between a plurality of frames before a current frame falls within a predetermined range, the control section determines that the radiation dose is stable.

4. The radiographic imaging apparatus according to claim 1, wherein, when an inclination of a difference in radiation dose information between an immediately preceding frame and a current frame falls within a predetermined range, the control section determines that the radiation is stable.

5. The radiographic imaging apparatus according to claim 1, wherein, until the radiation dose becomes stable, the control section obtains the radiation dose information at settings of a higher frame rate and a higher sensitivity than after the radiation dose becomes stable and outputs no image.

6. The radiographic imaging apparatus according to claim 1, wherein the control section outputs no image until the radiation dose becomes stable, and after the radiation does becomes stable, the control section determines the image capturing condition and outputs an image captured after the image capturing condition is determined.

7. The radiographic imaging apparatus according to claim 1, wherein the control section determines the image capturing condition based on radiation dose information after a lapse of a predetermined time after determining to start an emission of radiation based on the radiation dose information.

8. The radiographic imaging apparatus according to claim 1, wherein the control section determines the image capturing condition based on radiation dose information when receiving information based on a user's operation.

9. The radiographic imaging apparatus according to claim 1, wherein the control section determines the image capturing condition based on image information based on the electrical signals converted by the plurality of pixels.

10. The radiographic imaging apparatus according to claim 9, wherein the control section determines the image capturing condition based on pixel values of a target region in the image information based on the electrical signals converted by the plurality of pixels.

11. The radiographic imaging apparatus according to claim 10, wherein the control section determines the image capturing condition based on the pixel values of the target region when the pixel values of the target region have become stable.

12. The radiographic imaging apparatus according to claim 9, wherein the control section determines, as the image capturing condition, a sensitivity, an accumulation time, a frame rate, or a number of images to be captured.

13. The radiographic imaging apparatus according to claim 9, wherein, when a difference in the image information between a plurality of frames before a current frame falls within a predetermined range, the control section determines that the image information has become stable.

14. A radiographic imaging system comprising:

a radiographic imaging apparatus comprising a plurality of pixels configured to convert radiation to electrical signals and a control section configured to determine an image capturing condition based on the electrical signals converted by the plurality of pixels and to start image capturing; and a radiation source configured to emit radiation, wherein the control section further determines the image capturing condition based on incident-radiation dose information based on the electrical signals converted by the plurality of pixels, and wherein the control section further determines the image capturing condition based on radiation dose information when a radiation dose has become stable.

15. A method for controlling a radiographic imaging apparatus including a plurality of pixels configured to convert radiation to electrical signals, the method comprising:

determining, based on a stabilization of incident-radiation dose information based on the electrical signals converted by the plurality of pixels, an image capturing condition, and starting image capturing, wherein the image capturing condition is further determined based on the incident-radiation dose information based on the electrical signals converted by the plurality of pixels, and wherein the image capturing condition is further determined based on radiation dose information when a radiation dose has become stable.

* * * * *